United States Patent [19]

Mongelli et al.

[11] Patent Number: 5,332,756
[45] Date of Patent: Jul. 26, 1994

[54] 3-DEOXY-MANNOSAMINE DERIVATIVES

[75] Inventors: Nicola Mongelli; Alberto Bargiotti; Nuccia Oneto; Cristina Geroni, all of Milan, Italy

[73] Assignee: Farmitalia Carlo Erba S.R.L., Milan, Italy

[21] Appl. No.: 922,229

[22] Filed: Jul. 31, 1992

[30] Foreign Application Priority Data

Aug. 6, 1991 [GB] United Kingdom ............... 9116896

[51] Int. Cl.$^5$ ...................... A01N 43/16; C07H 5/04; C07H 5/06
[52] U.S. Cl. ................. 514/459; 536/18.7; 536/55.2
[58] Field of Search ............... 536/55.2, 18.7; 514/8; 530/322

[56] References Cited

U.S. PATENT DOCUMENTS 4,216,208  8/1980  De Barbieri .................. 574/8
4,647,453  3/1987  Meisner ........................ 424/54

FOREIGN PATENT DOCUMENTS 0385287  9/1990  European Pat. Off.

OTHER PUBLICATIONS

Cerny et al., Collection Czechoslovak Chem. Commun., vol. 48, 1983, pp. 2386-2394.
Pan et al., J. of Biol. Chem., 267(13), 8991-8999, 1992.
Bernacki et al., Cancer Research, 45, pp. 695-702, 1985.
Arita et al., Bull. Chem. Soc. of Japan, vol. 45, 3614-3619, 1972.
Cerny et al., Coll. Czech. Chem. Commun., vol. 49, 1984.
Hasegawa et al., Carbohydrate Research., 79(1980), 255-264.
Jegou et al., Carbohydrate Research., 45(1975), 323-326.
Lambert et al., Chem. Ber., 93, 2915-23, 1960.
J. Org. Chem., vol. 26, pp. 2455-2458, Jul., 1961, W. Roth, et al., "Methyl Derivatives of D-Mannosamine".
Agr. Biol. Chem, vol. 47, No. 4, pp. 839-846, 1983, H. Okumura, et al., "The Behavior of Some 2-Acetamido-2-Deoxy-Furanoses in the Presence of Alkaline Ion-Exchange Resin".
Carbohydrate Research, vol. 38, pp. 205-216, 1974, Nasir-Ud-Din, et al., "Synthesis of the 6-Methyl and 3,6-and 4,6-Dimethyl Ethers of Methyl 2-Acetamido-2-Deoxy-alpha-d-Mannopyranoside".
J. Chem. Res., pp. (M).0186-0196, 1982, J. R. Pougny, et al., "(3S,4S)-4-Methylheptan-3-ol, A Pheromone, Component of the Smaller European Elm Bark Bettle: Synthesis Form D-Glucose".
Nasir-Ud-Din et al, "Synthesis of the 3-and 4-methyl, 3,4-dimethyl, and 3,4,6-trimethyl ethers of methyl 2-acetamido-2-deoxy-alpha-D-mannopyranoside", Carbohydrate Research, vol. 28, No. 2, Jun. 1 1973, Amsterdam, Netherlands, pp. 243-251.

Primary Examiner—David M. Naff
Assistant Examiner—Michael V. Meller
Attorney, Agent, or Firm—Oblon, Spivak, McClelland, Maier & Neustadt

[57] ABSTRACT

The present invention relates to 3-deoxy-derivatives of D-mannosamine of formula

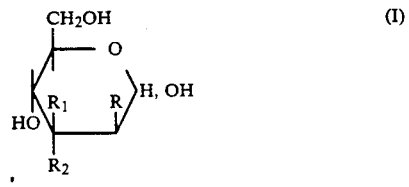

wherein R is $-NH_2$ or a $C_{2-5}$ alkanoyl-NH— or $CF_3CONH-$ group; each of $R_1$ and $R_2$ independently is $C_1-C_4$ alkyl, or $R_1$ is hydrogen, halogen, $C_1-C_4$ alkyl or $C_1-C_4$ alkoxy, and $R_2$ is hydrogen or both of $R_1$ and $R_2$ are fluorine; and wherein, when $R_1$ is methoxy and $R_2$ is hydrogen then R is other than $-NH_2$, or a pharmaceutically acceptable salt thereof, which are useful as angiogenesis inhibitors, in particular as development of metastasis inhibitors.

5 Claims, No Drawings

3-DEOXY-MANNOSAMINE DERIVATIVES

The present invention relates to 3-deoxy-derivatives of D-mannosamine, to a process for their preparation, to pharmaceutical compositions containing them and to their use in therapy.

The present invention provides, as a first object, new compounds having the following formula (I)

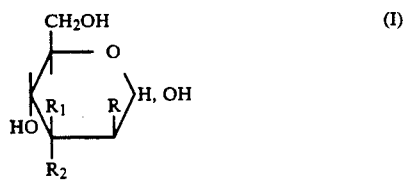

wherein R is —NH$_2$ or a C$_2$-C$_5$ alkanoyl-NH— or CF$_3$CONH— group; each of R$_1$ and R$_2$ independently is C$_1$-C$_4$ alkyl, or R$_1$ is hydrogen, halogen, C$_1$-C$_4$ alkyl or C$_1$-C$_4$ alkoxy, and R$_2$ is hydrogen or both of R$_1$ and R$_2$ are fluorine; and wherein, when R$_1$ is methoxy and R$_2$ is hydrogen then R is other than —NH$_2$, and the pharmaceutically acceptable salts thereof.

From the above formula (I) it appears clear that the hydroxyl group attached to C-1 may be either below or above the plane of the ring. Accordingly, the present invention includes within its scope both the α and β anomeric forms and the mixtures thereof of the compounds of the invention, Objects of the present invention are also the metabolites and the metabolic precursors or bio-precursors (otherwise known as pro-drugs) of the compounds of formula (I).

The alkyl, alkoxy and alkanoyl groups may be a branched or straight chain groups, preferably they are straight chain groups.

A C$_1$-C$_4$ alkyl group is e.g. methyl, ethyl, propyl or isopropyl, preferably methyl or ethyl, in particular methyl. C$_1$-C$_4$ alkoxy group is e.g. methoxy, ethoxy or propoxy, preferably methoxy or ethoxy.

A C$_2$-C$_5$ alkanoyl group is preferably an acetyl group.

A halogen atom is e.g. fluorine or iodine.

The compounds of the present invention in which R is —NH$_2$ can be salified.

Pharmaceutically acceptable salts of the compounds of the invention include acid addition salts, with inorganic, e.g. nitric, hydrochloric, hydrobromic, sulphuric, perchloric and phosphoric acids, or organic, e.g.-acetic, propionic, glycolic, lactic, oxalic, malonic, malic, maleic, tartaric, citric, benzoic, cinnamic, mandelic and salicylic acids.

As stated above the present invention also includes within its scope pharmaceutically acceptable bio-precursors (otherwise known as pro-drugs) of the compounds of formula (I), i.e. compounds which have a formula different from formula (I) above but which are converted directly or indirectly in vivo into a compound of formula (I).

The above proviso excludes from the scope of formula (I) the compound 2-amino-2-deoxy-3-0-methyl-D-mannopyranose hydrochloride which is known from J. Org. Chem. Vol. 26, pp. 2455-2458 (1961), however no biological activity is therein described for such compounds.

Accordingly a further object of the present invention is to provide a pharmaceutical composition comprising, as an active agent, a compound of formula (I)

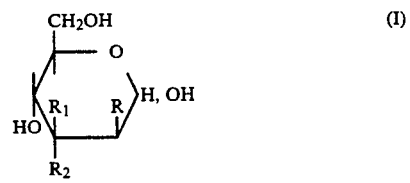

wherein
R is —NH$_2$ or a C$_2$-C$_5$ alkanoyl-NH— or CF$_3$CONH— group; each of R$_1$ and R$_2$, independently, is C$_1$-C$_4$ alkyl, or R$_1$ is hydrogen, halogen, C$_1$-C$_4$ alkyl or C$_1$-C$_4$ alkoxy and R$_2$ is hydrogen or both of R$_1$ and R$_2$ are fluorine or a pharmaceutically acceptable salt thereof and a pharmaceutically acceptable carrier and/or diluent.

The new compounds of formula (I) and the active principle of the pharmaceutical compositions, according to the present invention, are herein termed "the compounds of the invention".

Preferred compounds of the invention are the compounds of formula (I), wherein, subject to the above proviso R is —NH$_2$ or a C$_2$-C$_5$ alkanoyl-NH— group;
each of R$_1$ and R$_2$, independently is C$_1$-C$_4$ alkyl, or
R$_1$ is hydrogen, halogen, C$_1$-C$_4$ alkyl or C$_1$-C$_4$ alkoxy and
R$_2$ is hydrogen or both of R$_1$ and R$_2$ are fluorine; and the pharmaceutically acceptable salts thereof.

Specific examples of preferred new compounds according to the present invention are the following:
2-amino-2,3-dideoxy-D-mannopyranose;
2-acetamido-2,3-dideoxy-D-mannopyranose;
2-amino-2,3-dideoxy-3-iodo-D-mannopyranose;
2-acetamido-2,3-dideoxy-3-iodo-D-mannopyranose;
2-acetamido-2-deoxy-3-0-methyl-D-mannopyranose;
2-amino-2,3-dideoxy-3-fluoro-D-mannopyranose;
2-acetamido-2,3-dideoxy-3-fluoro-D-mannopyranose;
2-amino-2,3-dideoxy-3-C-methyl-D-mannopyranose;
2-acetamido-2,3-dideoxy-3-C-methyl-D-mannopyranose;
2-amino-2,3-dideoxy-3-C-ethyl-D-mannopyranose;
2-acetamido-2,3-dideoxy-3-C-ethyl-D-mannopyranose;
2-amino-2,3-dideoxy-3,3-C-dimethyl-D-mannopyranose;
2-acetamido-2,3-dideoxy-3,3-C-dimethyl-D-mannopyranose;
2-amino-2,3-dideoxy-3,3-difluoro-D-mannopyranose;
2-acetamido-2,3-dideoxy-3,3-difluoro-D-mannopyranose;
and, if the case, the pharmaceutically acceptable salts thereof, in particular the hydrochloride.

The compounds of the invention and the salts thereof can be obtained by a process comprising:
a) hydrolysing a compound of formula (II)

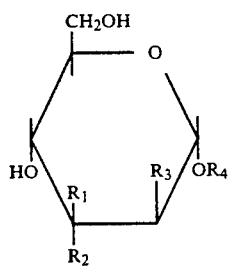

wherein
$R_1$ and $R_2$ are as defined above, $R_3$ is an acyl-NH— group and
$R_4$ is a hydroxy-protecting group, thus obtaining a compound of formula (I) in which R is —$NH_2$; or b) hydrolysing a compound of formula (III)

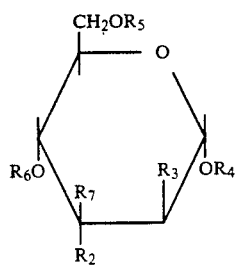

wherein $R_7$ is fluorine, $R_2$ is hydrogen or fluorine, $R_3$ and $R_4$ are as defined above and $R_5$ and $R_6$, taken together, form a protective group of the C-4 and C-6 hydroxylic groups, thus providing a compound of formula (I) in which R is —$NH_2$, $R_1$ is fluorine and $R_2$ is hydrogen or fluorine; or c) acylating a compound of formula (IV)

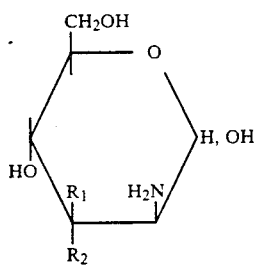

wherein $R_1$ and $R_2$ are as defined above, thus obtaining a compound of formula (I) in which R is a $C_2$-$C_5$ alkanoyl-NH— or $CF_3$—CONH— group; and, if desired, converting a compound of formula (I) into another compound of formula (I), and/or, if desired, salifying a compound of formula (I), and/or, if desired obtaining a free compound from a salt thereof.

The hydrolysis of a compound of formula (II) or (III) as well as the acylation of a compound of formula (IV) are analogy processes that can be carried out according to known methods from the chemistry of carbohydrates. Therefore the following description of processes a), b) and c), above, is meant to provide a preferred way as how to carry out such processes, without limiting the scope of the present invention.

In a compound of formula (II) or of formula (III) $R_3$ as an acyl-NH— group is for example a $C_2$-$C_5$ alkanoyl-NH— group, typically —$NHCOCH_3$ or —$NHCOCF_3$, or a benzyloxycarbonyl-NH— group.

When in a compound of formula (II) $R_1$ is iodine, then $R_3$ is preferably a —$NHCOCF_3$ group, whereas when $R_1$, being as defined above, is other than iodine, then $R_3$ is preferably a $C_2$-$C_5$ alkanoyl-NH-group, in particular —$NHCOCH_3$.

In a compound of formula (II) or of formula (III) $R_4$ as an hydroxy-protecting group is for instance a $C_1$-$C_4$ alkyl group, typically methyl, ethyl or isopropyl, or a benzyl group.

When in a compound of formula (III) $R_5$ and $R_6$, taken together, form a protective group of the C-4 and C-6 hydroxylic groups, such protective group may be one usually employed in the chemistry of sugars, typically a benzilydene group.

The hydrolysis of a compound of formula (II) or of formula (III) can be performed by treatment with a mineral acid, e.g. HCl or $H_2SO_4$. Preferably the reaction is carried out by treatment with 5N HCl or 2.5% $H_2SO_4$, at a temperature ranging from about 50° C. to about 110° C.

The acylation of a compound of formula (IV) can be performed by treatment with a suitable acylating agent, for instance a suitable anhydride. For example, if a compound of formula (I) wherein R is a —$NHCOCH_3$ group is desired, a compound of formula (IV) is reacted with acetic anhydride, in a lower alkanol, preferably methanol, at room temperature.

As stated above a compound of formula (I) can be converted into another compound of formula (I). Acylation of a compound of formula (IV) can be regarded as an example of such optional convertion. In fact a compound of formula (IV) is a compound of formula (I) wherein R is $NH_2$.

The salification of a compound of formula (I), in which R is —$NH_2$, can be carried out by known methods in the art.

The compounds of formula (II) which are either known or new compounds can be obtained by known methods.

For instance, a compound of formula (II), wherein $R_1$ and $R_2$ are hydrogen, $R_3$ is —$NNCOCH_3$ and $R_4$ is methyl, can be obtained according to the method described in Agr.Biol.Chem., 33(5), 748–754(1969). Analogously, a compound of formula (II) wherein $R_1$ is methoxy, $R_2$ is hydrogen, $R_3$ is —$NHCOCH_3$ and $R_4$ is methyl can also be obtained by following the process described in Carbohydrates Research, 38, 205–216(1974).

According to the general method provided by the present invention, a compound of formula (II) can be obtained by removal of the C-4 and C-6 hydroxy-protecting groups in a compound of formula (V)

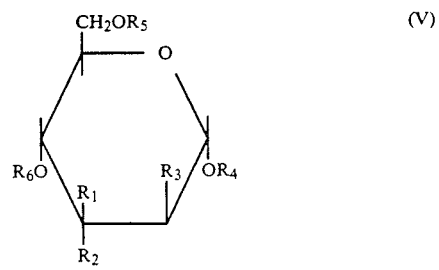

wherein $R_1$, $R^2$, $R_3$, $R_4$, $R_5$ and $R_6$ are as defined above, through hydrolysis. Preferably such hydrolysis is a mild-conditions hydrolysis with a mineral acid e.g. HCl or $H_2SO_4$, for instance as described in Tetrahedron Letters, 18, 2271(1968). The compounds of formula (III) which are new are compounds of formula (V) wherein $R_1$, being as defined above, is fluorine, $R_2$ is hydrogen or fluorine and $R_4$, $R_5$ and $R_6$ are as defined in formula (V).

A compound of formula (V), wherein $R_1$, being as defined above, is other than iodine, can be obtained by acylating a compound of formula (VI)

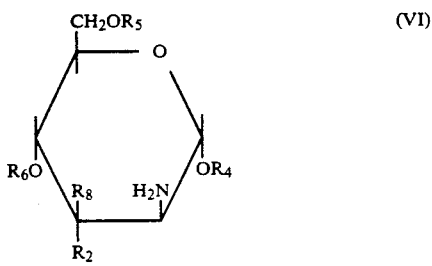

wherein $R_2$, $R_4$, $R_5$ and $R_6$ are as defined above and $R_8$ is as $R_1$ defined above except iodine.

The acylation of a compound of formula (VI) can be carried out by following the same reaction conditions described above as to the acylation of a compound of formula (IV).

A compound of formula (V) wherein $R_1$ is iodine and $R_2$, $R_3$, $R_4$, $R_5$ and $R_6$ are as defined above can be obtained from a compound of formula (VII)

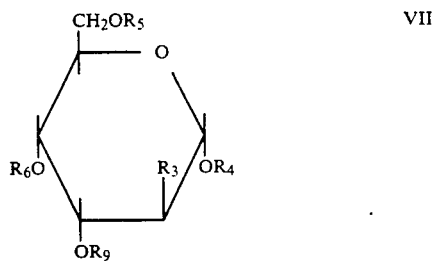

wherein $R_3$, $R_4$, $R_5$ and $R_6$ are as defined above and $R_9$ is a good leaving group e.g. tosyl, mesyl or trifluoromethanesulfonyl, preferably tosyl, by treatment with an alkali metal iodide, preferably an excess of NaI, in a ketone e.g. dimethylketone, at reflux temperature.

The compounds of formula (VII) can be obtained according to known methods from the corresponding C-3 hydroxy derivatives, which are either known or can be obtained by known methods from known compounds.

A compound of formula (VI) can be obtained by reducing a compound of formula (VIII)

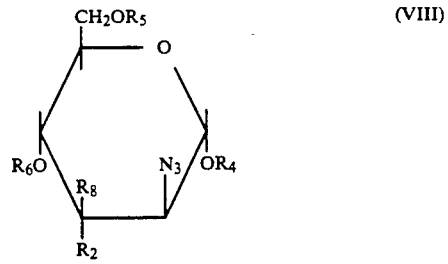

wherein $R_2$, $R_4$, $R_5$, $R_6$ and $R_8$ are as defined above.

Reduction of a compound of formula (VIII) can be obtained by known methods, for instance by catalytic hydrogenation, preferably with 10% Pd/C as catalyst, at a pressure ranging from about 10 to about 20 atmospheres.

A compound of formula (VIII), wherein $R_2$ and $R_8$, being as defined above, are other than fluorine can be obtained from a compound of formula (IX)

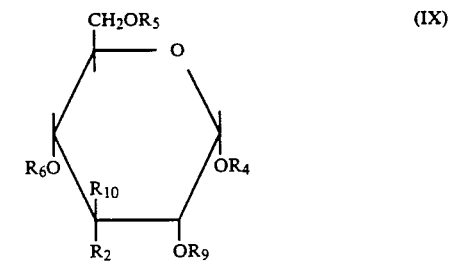

wherein
each of $R_{10}$ and $R_2$ independently is $C_1$-$C_4$ alkyl, or R10 is hydrogen, $C_1$-$C_4$ alkyl or $C_1$-$C_4$ alkoxy and $R_2$ is hydrogen, and
$R_4$, $R_5$, $R_6$ and $R_9$ are as defined above, by treatment with a suitable azido derivative, e.g. sodium azide.

The reaction of a compound of formula (IX) with sodium azide can be carried out e.g. in dimethylformamide by reaction with an excess of sodium azide at reflux temperature.

A compound of formula (VIII) wherein $R_8$ is fluorine and $R_2$ is hydrogen can be obtained as described in J. Org. Chem. 51, 4558–4564(1986). Alternatively it can be obtained from a compound of formula (X)

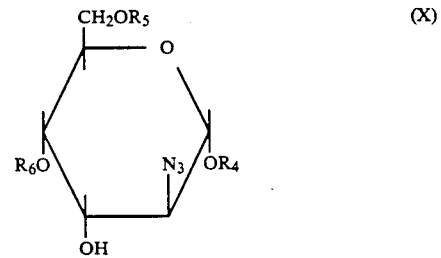

wherein $R_4$, $R_5$ and $R_6$ are as defined above, by treatment with diethylaminosulfurtrifluoride (DAST), in dichloroethylene, at room temperature.

A compound of formula (VIII) wherein $R_2$ and $R_8$ are fluorine can be obtained by oxidation of a compound of formula (X), as defined above, and subsequent treatment of the ketone compound thus obtained, with DAST in dry benzene at room temperature.

The compounds of formula (X) are known compounds or can be obtained by known methods from known compounds. The compounds of formula (IX) wherein $R_2$ and $R_{10}$ are as defined above can be obtained according to known methods from the corresponding C-2 hydroxy derivatives, which are either known or can be obtained from known compounds.

For example a C-2 free hydroxy derivative of a compound of formula (IX), wherein $R_2$ and $R_{10}$ are $C_1$-$C_4$ alkyl, or $R_{10}$ is hydrogen or $C_1$-$C_4$ alkyl and $R_2$ is hydrogen, can be obtained by reducing a compound of formula (XI)

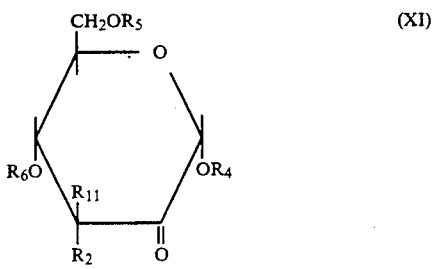

wherein $R_4$, $R_5$ and $R_6$ are as defined above and $R_2$ and $R_{11}$ are $C_1$-$C_4$ alkyl or $R_{11}$ is hydrogen or $C_1$-$C_4$ alkyl and $R_2$ is hydrogen, by treatment with a suitable reducing agent e.g. $LiAlH_4$, according to known methods.

A compound of formula (IX) wherein $R_{10}$ is $C_1$-$C_4$ alkoxy and $R_2$ is hydrogen and $R_4$, $R_5$ and $R_6$ are as defined above can be obtained for instance from a compound of formula (XII)

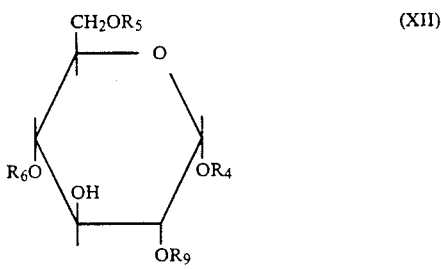

wherein $R_4$, $R_5$, $R_6$ and $R_9$ are as defined above, according to known methods, for instance by reaction with a suitable $C_1$-$C_4$ alkyl-halide, in particular the iodide, in the presence of $Ag_2O$.

The compounds of formula (XI) wherein $R_2$ and $R_{11}$ are both hydrogen and $R_4$, $R_5$ and $R_6$ are as defined above, are known or may be obtained as described in Agr. Biol. Chem. 33(5), 748-754(1969).

The compounds of formula (XI) wherein $R_2$ and $R_{11}$ are both $C_1$-$C_4$ alkyl can be obtained by alkylating another compound of formula (XI) wherein $R_2$ and $R_{11}$ are both hydrogen.

The alkylation of a compound of formula (XI), wherein $R_2$ and $R_{11}$ are both hydrogen, so as to provide new compounds of formula (XI), wherein $R_2$ and $R_{11}$ are both methyl and $R_4$, $R_5$ and $R_6$ are as defined above, can be obtained by treatment with methyl iodide and sodium hydride, in anhydrous dimethyl formamide at room temperature.

The compounds of formula (XI) wherein $R_{11}$ is $C_1$-$C_4$ alkyl and $R_2$ is hydrogen can be obtained for instance according to the method described in J.Chem.res. (M). 0186-0196 (1982).

The compounds of formula (XII) are either known compounds or can be obtained by known methods from known compounds.

The compounds of formula (II), in which each of $R_1$ and $R_2$ independently is $C_1$-$C_4$ alkyl; or $R_1$ is halogen, $C_1$-$C_4$ alkyl and $R_2$ is hydrogen; or both $R_1$ and $R_2$ are fluorine and $R_3$ $R_4$ are as defined above are new and are a further object of the present invention.

A further object of the present invention are also the compounds of formula (III), as herein defined, which are new.

PHARMACOLOGY

The compounds of the invention have been found to be active as angiogenesis inhibitors and in particular as development of metastasis inhibitors.

An anglogenesis inhibitor is an agent capable of suppressing the growth of new blood vessels. Therefore the compounds of the present invention are useful in treating several pathological conditions in mammals, where the growth of new blood vessels is detrimental, for example in chronic inflammation, diabetic retinopathy, psoriasis, rheumatoid arthritis, tumor growth and development of metastasis.

In particular, in cancer therapy the compounds of the invention can be administered alone or in association with antitumor agents such as doxorubicin, etoposide, fluorouracil, mephalan, cyclophosphamide, bleomycin, vinblastin or mitomycin. The angiogenesis inhibitor activity of the compounds of the present invention is shown e.g. by the fact that they have been found to be active in the chorioallantoic membrane test, according to the Folkman's method [Nature, 297, 307 (1982)].

The activity of the compoundsd of the invention in inhibiting in particular the development of metastasis is proven also by their activity against induction in mouse of experimental metastasis. Accordingly the representative compound of the invention 2-acetamido-2,3-dideoxy-D-mannopyranose was tested against induction in mouse of experimental metastasis of B16F10 melanoma cell line.

B16F10 cells ($5.10^{-4}$) were injected into the tail vein of C3H mice on day 0.

The tested compound was administered daily six times starting from day 1. Animals were sacrified on day 14 and the lung metastasis counted. Control animals have an average of 47 metastatic loci (35-57) and treated animals 0 (0-2).

The compounds of the invention can be administered by the usual routes, for example, parenterally, e.g. by intravenous injection or infusion, intramuscularly, subcutaneosly, topically or orally.

The dosage depends on the age, weight and conditions of the patient and on the administration route.

The pharmaceutical composition of the invention may contain a compound of the invention, as the active substance, in association with one or more pharmaceutically acceptable excipients and/or carriers.

Specific preferred examples of compounds of the invention to be used as an active substance in the preparation of a pharmaceutical composition according to the present invention are the following:

2-amino-2-deoxy-3-0-methyl-D-mannopyranose;
2-amino-2,3-dideoxy-D-mannopyranose;
2-acetamido-2,3-dideoxy-D-mannopyranose;
2-amino-2,3-dideoxy-3-iodo-D-mannopyranose;
2-acetamido-2,3-dideoxy-3-iodo-D-mannopyranose;
2-acetamido-2-deoxy-3-0-methyl-D-mannopyranose;

2-amino-2,3-dideoxy-3-fluoro-D-mannopyranose;
2-acetamido-2,3-dideoxy-3-fluoro-D-mannopyranose;
2-amino-2,3-dideoxy-3-C-methyl-D-mannopyranose;
2-acetamido-2,3-dideoxy-3-C-methyl -D-mannopyranose;
2-amino-2,3-dideoxy-3-C-ethyl-D-mannopyranose;
2-acetamido-2,3-dideoxy-3-C-ethyl-D-mannopyranose;
2-amino-2,3-dideoxy-3,3-C-dimethyl-D-mannopyranose;
2-acetamido-2,3-dideoxy-3,3-C-dimethyl-D-mannopyranose;
2-amino-2,3-dideoxy-3,3-difluoro-D-mannopyranose;
2-acetamido-2,3-dideoxy-3,3-difluoro-D-mannopyranose;
and, if the case, the pharmaceutically acceptable salts thereof; in particular the hydrochloride.

The pharmaceutical compositions of the invention are usually prepared following conventional methods and are administered in a pharmaceutically suitable form.

For instance, solutions for intravenous injection or infusion may contain as carried, for example, sterile water or preferably, they may be in the form of sterile aqueous isotonic saline solutions.

Suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

In the forms for topical application, e.g. creams, lotions or pastes for use in dermatological treatment, the active ingredient may be mixed with conventional oleoginous or emulsifying excipients.

The solid oral forms, e.g. tablets and capsules, may contain, together with the active compound, diluents, e.g. lactose, dextrose, saccharose, cellulose, corn starch and potato starch; lubricants, e.g. silica, talc, steric acid, magnesium or calcium stearate, and/or polyethylene glycols; binding agents, e.g. starches, arabic gums, gelatin, methylcellulose, carboxymethyl cellulose, polyvinylpyrrolidone; disaggregating agents, e.g. a starch, alginic acid, alginates, sodium starch glycolate; effervescing mixtures; dyestuffs; sweeteners; vetting agents, for instance, lecithin, polysorbates, lauryl sulphates; and, in general, non-toxic and pharmacologically inactive substances used in pharmaceutical formulations. These pharmaceutical preparations may be manufactured in a known manner, for example by means of mixing, granulating, tabletting, sugar-coating, or film-coating processes.

Furthermore, according to the invention there is provided a method of treating pathological conditions where the growth of new blood vessels is detrimental, for example chronic inflammation, diabetic retinopathy, psoriasis, rheumatoid arthritis, tumors and development of metastasis, in mammals in need thereof, comprising administering to the said mammals a composition of the invention.

Object of the present invention are also products containing a compound of the invention, or a pharmaceutically acceptable salt thereof, and one or more antitumor agents, as a combined preparation for simultaneous, separate or sequential use in cancer therapy.

The term "combined" method of treatment is meant to include both separate and substantially contemporaneous administration of a composition containing a compound of formula (I), or a pharmaceutically acceptable salt thereof, and a pharmaceutically composition containing a different pharmaceutically active agent.

Agents, that can be formulated with a compound of the invention or alternatively, can be administered in a combined method of treatment depend on the disease state to be cured and are, for instance, doxorubicin, etoposide, fluoruaracil mephalan, cyclophosphamide, bleomycin, vinblastin and mitomycin.

The following examples illustrate but do not limit the invention.

EXAMPLE 1

2-amino 2,3-dideoxy-3-iodo-D-mannopyranose hydrochloride (compound I, $R=NH_2$; $R_1=I$; $R_2=H$)

To a solution of hydrochloric acid 5N (150 ml) is added methyl 2,3-dideoxy-3-iodo-2-trifluoroacetamido-D-mannopyranose (1 g). The solution is heated for 2 hours at 100° C. The aqueous phase is decolorized with activated carbon and evaporated.

Addition to and evaporation from the resulting syrup from methanol yields 0.5 g of the title compound as white cristalline powder: m.p. 122°-123° C.; $[\alpha]_D^{25} = -7.5$ (c.1,H$_2$O); IR (KBr) $\nu$ 3400-3200$^{cm-1}$ (OH, NH$_3^+$), 2130, 1630 and 1500$^{cm-1}$ (NH$_3^+$).

By proceeding analogously the following compounds can be obtained as hydrochloride:
2-amino-2,3-dideoxy-D-mannopyranose;
2-amino-2,3-dideoxy-3-fluoro-D-mannopyranose;
2-amino-2,3-dideoxy-3-C-methyl-D-mannopyranose;
2-amino-2,3-dideoxy-3-C-ethyl-D-mannopyranose;
2-amino-2,3-deoxy-3,3-C-dimethyl-D-mannopyranose;
2-amino-2,3-dideoxy-3,3-difluoro-D-mannopyranose;
and
2-amino-2-deoxy-3-0-methyl-D-mannopyranose, $[\alpha]_D^{20} = -23.3°$ final (C,5,water) .

EXAMPLE 2

Methyl 2,3-dideoxy-3-iodo-2-trifluoroacetamido-D-mannopyranose (compound II, $R_1=I$; $R_2=H$; $R_3=NHCOCF_3$; $R_4=CH_3$)

A solution of methyl-4,6-0-benzylidene-2,3-dideoxy-3-iodo-2-trifluoroacetamido-α-D-mannopyranoside in 0.5N methanolic hydrogen chloride (50 ml) is stirred for 2 hours at 20° C., then concentrated to half volume and diluted with ether. The product (1,2 g) of the title compound (as white solid) is washed with dry ether and evaporated in vacuo.

FD-MS 399 (H+); m.p. 171°-172° C. (with decomposition).

EXAMPLE 3

Methyl 4,6-0-benzylidene-2,3-dideoxy-3-iodo-2-trifluoroacetamido-α-D-mannopyranose (compound V, $R_1=I$; $R_2=H$; $R_3=NHCOCF_3$; $R_4=CH_3$; $R_5+R_6=$benzylidene group)

Methyl -4,6-0-benzylidene-2-deoxy-3-0-p.toluensulfonyl-2-trifluoroacetamido-α-D-mannopyranose (1.5 g) is dissolved in 70 ml of dry butanone with sodium iodide (2 g). The mixture is refluxed for 1 hour and concentrated.

The residue is extracted with methylene chloride and washed with water to neutrality and then concentrated to dryness. Crystallization of the residue from ethyl ether and hexane gives 2.0 g of the title compound: m.p. 152°–153° C. (with decomposition).

EXAMPLE 4

2-acetamido 2,3-dideoxy-D-mannopyranose. (Compound I, R=NHCOCH$_3$; R$_1$=R$_2$=H)

Amino 2,3-dideoxy-D-mannopyranose (0.8 g) is dissolved in dry methanol (30 ml) and acetic anhydride (3 ml); the mixture is stirred overnight.

Evaporation of the solvent gives a crystalline mass which is recrystallized from ethanol-acetone to give 0.60 g of the title compound: m.p. 140°–142° C., $[\alpha]_D^{25} = -4.5$ (c,0.1,H$_2$O). By proceeding analogously the following compounds can be obtained:
2-acetamido-2,3-dideoxy-3-iodo-D-mannopyranose;
2-acetamido-2-deoxy-3-0-methyl-D-mannopyranose;
2-acetamido-2,3-dideoxy-3-fluoro-D-mannopyranose:

1H-NMR (200 MHz, DMSO-d6):1.86 (s.3H, CH$_3$-CONH); 3.4–3.8 (m, 4H, H-4, H-5, CH$_2$—OH); 4.25 (m, 1H, H-2); 4.48 ( t, J=6.1 Hz , 1H , CH$_2$—OH); 4.60 (ddd, J=5.4, 10.3 Hz, J$_{H-F}$=50.0 Hz, 1H, H-3); 4.85 (ddd, J=1.9, 4.3 Hz, J$_{H-F}$=5.6 Hz, 1H, H-1); 5.31 (d, J=5.7 Hz, 1H, OH-4); 6.73 (d,J=4.3 Hz, 1H, OH-1); 7.46 (d,J=8.9 Hz, 1H, NH-COCH$_3$).
2-acetamido-2,3-dideoxy-3-C-methyl-D-mannopyranose;
2-acetamido-2,3-dideoxy-3-C-ethyl-D-mannopyranose;
2-acetamido-2,3-dideoxy-3,3-C-dimethyl-D-mannopyranose and
2-acetamido-2,3-dideoxy-3,3-difluoro-D-mannopyranose.

EXAMPLE 5

Methyl-2-acetamido-2,3-dideoxy-D-mannopyranose (Compound II, R$_1$=R$_2$=H; R$_3$=NHCOCH$_3$; R$_4$=CH$_3$)

A solution of methyl-2-acetamido-4,6-0-benzylidene-2,3-dideoxy-α-mannopyranose (2 g, 7.06 mmol) in dry methanol (50 ml) is stirred with acetyl chloride (0.6 ml) for 4h at 20° C., and then neutralized with sodium hydrogen carbonate, filtered and concentrated.

The residue is extracted with hexane to remove benzaldehyde, and then with acetone to give 1.47 g (95%) of methyl-2-acetamido-2,3-dideoxy-α-D-mannopyranose as an oil.

$^1$H-NMR (200 MHz, CDCl$_3$): 2.03 (s, 3H, CH$_3$-CO-NH); 2.12 (m, 2H, CH$_2$-3); 3.40 (s, 3H, CH$_3$O); 3.68 (m, 1H, H-4); 3.75 (dd, J=10.0, 10.0-Hz, 1H,CH-(H)-6); 3.88 (ddd, J=4.0, 10.0, 10.0 Hz, 1H, H-5); 4.24 (dd, J=4.0, 10.0 Hz, 1H, CH-(H)-6); 4.31 (m, 1H, H-2); 4.50 (s, 1H, H-1); 5.56 (s, 1H, CH-Ph); 5.80 (d, J=7.6 Hz, 1H, NH-COCH$_3$); 7.3–7.5 (m, 5H, Ph)

EXAMPLE 6

Methyl-2-azido-4,6-0-benzylidene-2,3-dideoxy-3-fluoro-α-D-mannopyranoside (compound VIII , R$_2$=H, R$_4$=CH$_3$, R$_5$+R$_6$=benzylidene, R$_8$=F)

To a mixture of methyl-2-azido-4,6-0-benzylidene-α-D-altropyranoside (2 g) and 4-dimethylaminopyridine (DMAP) (1 g) in 40 ml of dry dichloromethane stirred at −20° C. under nitrogen, is slowly added 1 ml of diethylamino- sulfurtrifluoride (DAST).

The mixture is allowed to warm, and then is kept for 24 hours at room temperature.

After being cooled to −20° C., 20 ml of methanol is slowly added and the mixture is portioned between dichloromethane and aqueous sodium hydrogen carbonate solution. The organic phase is evaporated under reduced pressure and the residue is purified by chromatography, giving 1.25 g of the title compound: m.p. 122°–123° C.

EXAMPLE 7

Methyl 2-acetamido-4,6-0-benzylidene 2,3-dideoxy-3-fluoro-α-D-mannopyranoside (compound III, R$_2$=H; R$_3$=—NHCOCH$_3$; R$_4$=CH$_3$; R$_5$+R$_6$=benzylidene group)

To a solution of methyl-2-azido-4,6-0-benzylidene-2,3-dideoxy-3-fluoro-α-D-mannopyranoside (1 g) in methanol (100 ml) is added 10% Pd/C (1 g), and the mixture is hydrogenated at 10 atm. for 2 hours, filtered and then concentrated to dryness.

A solution of the resulting syrup in anhydrous pyridine (10 ml) is 0° C. is treated with acetic anhydride (5 ml). After 10 hours at room temperature the solution is poured into ice/water and the product extracted with dichloromethane.

The extract is successively washed with aqueous hydrogen carbonate and water and evaporated in vacuo.

Toluene (25 ml) is successively added to and evaporated from the residue.

Yield 1.15 g of the title compound: m.p. 85°–86° C.
$^1$H-NMR (200 MHz, C$_6$D$_6$): 1.56 (s, 3H, CH$_3$—CONH); 2.82 (s, 3H, CH$_3$O); 3.49 (dd, J=10.0, 10,0 Hz, 1H, CH(H)-6); 3.58 (ddd, J=9,6,10,0 Hz, J$_{H-F}$=10.0 Hz, 1H, H-4); 3.74 (ddd, J=4.4, 10.0, 10.0 Hz, 1H, H-5); 4.07 (ddd, J=4.6, 10,0 Hz , J$_{H-F}$=2.4 Hz, CH (H)-6); 4.63 (dd, J=1.1 Hz, J$_{H-F}$=4.0 Hz, 1H, H-1); 4.87 (m, 1H, H-2); 5.05 (ddd, J=5.4, 9.6 Hz, J$_{H-F}$=49.4 Hz. 1H, H-3); 5.20 (m, 1H, NH-COCH$_3$); 5.43 (s, 1H, CH-Ph); 7.1–7.7 (m, 5H, Ph)

EXAMPLE 8

Methyl-2-acetamido-2,3-dideoxy-3-fluoro-α-D-mannopyranose (compound II, R$_1$=F; R$_2$=H; R$_3$=NHCOCH$_3$; R$_4$=CH$_3$)

Methyl-2-acetamido-4,6-0-benzyliden-2,3-dideoxy-3fluoro-α-D mannopyranose (0.2 g) is dissolved in 0.5N methanolic hydrogen chloride (10 ml) and the solution is kept at room temperature for 3 hours.

Work-up gives the title compound as an oil (0.11 g).
$^1$H-NMR (200 MHz, DMSO-d6): 1.86 (s, 3H, CH$_3$-CONH); 3.23 (s, 3H, CH$_3$O); 3.2–3.8 (m, 4H, H-4, H-5, CH$_2$-OH; 4.35 (m, 1H, H-2); 4.49 (dd, J=1.4 Hz, J$_{H-F}$=4.8 Hz, H-1); 4.53 (ddd, J=5.2, 9.2 Hz, J$_{H-F}$=58.2 Hz, 1H, H-3); 4.61 (t,J=6.0 Hz, CH$_2$-OH); 5.41 (d, J=6.2 Hz, OH-4); 7.90 (d,J=8.8 Hz, NH-COCH$_3$

EXAMPLE 9

2-Amino-2,3-dideoxy-3-fluoro-D-mannopyranose

Methyl-2-acetamido 4,6-0-benzylidene 2,3-dideoxy-3-fluoro-α-D-mannopyranoside (1 g) is dissolved in 2.5% aqueous sulphuric acid (70 ml), and the solution is kept at 100° C. for 2 hours.

The aqueous solution is then neutralized with ion-exchange resin Dowex 1×2 (OH$^-$), evaporation of water in vacuo affords the title compound as a syrup.

IR (KBr) $\nu$ 3400–3200 cm$^1$ (OH, NH$_3^\oplus$) , 2130,1630 and 1500 cm$^1$ (NH$_3^\oplus$).

By proceeding analogously the amino-2,3-dideoxy-3,3-difluoro-D-mannopyranose can be obtained.

EXAMPLE 10

Tablets each weighing 0.150 g and containing 25 mg of the active substance, can be manufactured as follows:

| composition (for 10000 tablets): | |
|---|---|
| 2-acetamido-2,3-dideoxy-D-mannopyranose | 250 g |
| Lactose | 800 g |
| Corn starch | 415 g |
| Talc powder | 30 g |
| Magnesium stearate | 5 g |

The 2-acetamido-2,3-dideoxy-D-mannopyranose, the lactose and half the corn starch are mixed; the mixture is then forced through a sieve of 0.5 mm mesh size.

Corn starch (10 g) is suspended in warm water (90 ml) and the resulting paste is used to granulate the powder.

The granulate is dried, comminuted on a sieve of 1.4 mm mesh size, then the remaining quantity of starch, talc and magnesium stearate are added, carefully mixed and processed into tablets.

EXAMPLE 11

Capsules, each dosed at 0.200 g and containing 20 mg of the active substance can be prepared.

| Composition for 500 capsules: | |
|---|---|
| 2-acetamido-2.3-dideoxy-D-mannopyranose | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

We claim:

1. A compound of formula (I)

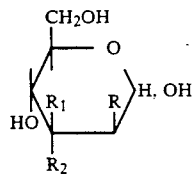

wherein

R is —NH$_2$ or a C$_2$–C$_5$ alkanoyl-NH— or CF$_3$CONH— group;

each of R$_1$ and R$_2$ independently is C$_1$–C$_4$ alkyl, or R$_1$ is hydrogen, halogen, C$_1$–C$_4$ alkyl or C$_1$–C$_4$ alkoxy, and R$_2$ is hydrogen or both of R$_1$ and R$_2$ are fluorine; and wherein, when R$_1$ is methoxy and R$_2$ is hydrogen then R is other than —NH$_2$, or a pharmaceutically acceptable salt thereof.

2. The compound of formula (I), according to claim 1, wherein, subject to the above proviso R is —NH$_2$ or a C$_2$–C$_5$ alkanoyl-NH— group;

each of R$_1$ and R$_2$, independently is C$_1$–C$_4$ alkyl, pr R$_1$ is hydrogen, halogen, C$_1$–C$_4$ alkyl or C$_1$–C$_4$ alkoxy and R$_2$ is hydrogen or both of R$_1$ and R$_2$ are fluorine; or a pharmaceutically acceptable salt thereof.

3. A compound selected from the group consisting of:
2-amino-2,3-dideoxy-D-mannopyranose;
2-acetamido-2,3-dideoxy-D-mannopyranose;
2-amino-2,3-dideoxy-3-iodo-D-mannopyranose;
2-acetamido-2,3-dideoxy-3-iodo-D-mannopyranose;
2-acetamido-2-deoxy-3-0-methyl-D-mannopyranose;
2-amino-2,3-dideoxy-3-fluoro-D-mannopyranose;
2-acetamido-2,3-dideoxy-3-fluoro-D-mannopyranose;
2-amino-2,3-dideoxy-3-C-methyl-D-mannopyranose;
2-acetamido-2,3-dideoxy-3-C-methyl-D-mannopyranose;
2-amino-2,3-dideoxy-3-C-ethyl-D-mannopyranose;
2-acetamido-2,3-dideoxy-3-C-ethyl-D-mannopyranose;
2-amino-2,3-dideoxy-3,3-C-dimethyl-D-mannopyranose;
2-acetamido-2,3-dideoxy-3,3-C-dimethyl-D-mannopyranose;
2-amino-2,3-dideoxy-3,3-difluoro-D-mannopyranose;
2-acetamido-2,3-dideoxy-3,3-difluoro-D-mannopyranose;
or, a pharmaceutically acceptable salt thereof.

4. A pharmaceutical composition comprising, as an active agent, a compound of formula (I)

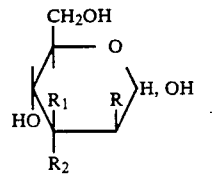

wherein

R is —NH$_2$ or a C$_2$–C$_5$ alkanoyl-NH— or CF$_3$CONH— group;

each of R$_1$ and R$_2$, independently, is C$_1$–C$_4$ alkyl, or R$_1$ is hydrogen, halogen, C$_1$–C$_4$ alkyl or C$_1$–C$_4$ alkoxy and R$_2$ is hydrogen or both of R$_1$ and R$_2$ are fluorine or a pharmaceutically acceptable salt thereof and a pharmaceutically acceptable carrier and/or diluent.

5. The pharmaceutical composition according to claim 4, wherein the active agent is selected from the group consisting of:
2-amino-2-deoxy-3-0-methyl-D-mannopyranose;
2-amino-2,3-dideoxy-D-mannopyranose;
2-acetamido-2,3-dideoxy-D-mannopyranose;
2-amino-2,3-dideoxy-3-iodo-D-mannopyranose;
2-acetamido-2,3-dideoxy-3-iodo-D-mannopyranose;
2-acetamido-2-deoxy-3-0-methyl-D-mannopyranose;
2-amino-2,3-dideoxy-3-fluoro-D-mannopyranose;
2-acetamido-2,3-dideoxy-3-fluoro-D-mannopyranose;
2-amino-2,3-dideoxy-3-C-methyl-D-mannopyranose;
2-acetamido-2,3-dideoxy-3-C-methyl-D-mannopyranose;
2-amino-2,3-dideoxy-3-C-ethyl-D-mannopyranose;
2-acetamido-2,3-dideoxy-3-C-ethyl-D-mannopyranose;
2-amino-2,3-dideoxy-3,3-C-dimethyl-D-mannopyranose;
2-acetamido-2,3-dideoxy-3,3-C-dimethyl-D-mannopyranose;
2-amino-2,3-dideoxy-3,3-difluoro-D-mannopyranose;
2-acetamido-2,3-dideoxy-3,3-difluoro-D-mannopyranose;
or a pharmaceutically acceptable salt thereof.

* * * * *